US00PP07875P

United States Patent [19]

Fruehwirth

[11] Patent Number: Plant 7,875

[45] Date of Patent: May 26, 1992

[54] POINSETTIA PLANT '293'

[75] Inventor: Franz Fruehwirth, Encinitas, Calif.

[73] Assignee: Paul Ecke Ranch, Inc., Encinitas, Calif.

[21] Appl. No.: 528,239

[22] Filed: May 24, 1990

[51] Int. Cl.[5] ..... A01H 5/00
[52] U.S. Cl. ..... Plt./86
[58] Field of Search ..... Plt./86, 86.4

[56] References Cited

U.S. PATENT DOCUMENTS

P.P. 7,275 7/1990 Fruewirth ..... Plt. 86
4,724,276 2/1988 Ecke, Jr. ..... 47/58

*Primary Examiner*—Howard J. Locker
*Attorney, Agent, or Firm*—Arnold, White & Durkee

[57] ABSTRACT

Poinsettia '293' is a self-branching cultivar with orange red flower bracts and excellent post-production keeping qualities. It has medium green foliage and a strong branching habit with large, stiff stems. The plant height is medium and the flowers have an erect bract presentation.

1 Drawing Sheet

BACKGROUND OF THE NEW PLANT

Poinsettia cultivar '293' is an induced mutant of a poinsettia seedling designated 'C-15'. The new cultivar is similar to 'C-15' in having thick, strong stems and an upright bract presentation. However, cultivar '293' shows unusally strong self-branching characteristics, often producing 8–10 strong axillary branches after pinching while the parent plant, 'C-15', typically produces only 3–4 axillary branches after pinching. The new cultivar is also somewhat shorter than 'C-15', a characteristic which in some markets is more commercially desirable in a house plant.

This new Poinsettia cultivar '293' originated as an induced mutation seedling designated as 'C-15' which resulted from cross pollination in my greenhouse in Encinitas, Calif. It was selected because of its prolific branching, erect bract presentation and excellent post-production lasting qualities; traits which distiguish it from other Poinsettia cultivars, and seem to make it a desirable plant for commercial greenhouse production. After selection, stem cuttings of this plant were vegetatively reproduced for test purposes in Encinitas, Calif., and clones of this plant were subjected to successive generations of vegetative propagation which demonstrated that its distinctive characteristics hold true from generation to generation.

DESCRIPTION OF THE PHOTOGRAPHS

Poinsettia '293' is illustrated in the accompanying color photographs. The upper photo is a side view of a pot with 3 unpinched plants in full flower. The lower photo is a top view of the same plants showing flower and bract formation.

DESCRIPTION OF THE PLANT

The following is a detailed description of this new Poinsettia as observed in my greenhouse in Encinitas, Calif., during December 1989. Observations were recorded from flowering plants, grown as 3 unpinched plants per pot. The pot was 14 cm. in diameter and 11 cm. in height. Color designations are compared to the 1986 edition of R.H.S. Colour Chart, first published in 1966 by The Royal Horticultural Society, London, England.

THE PLANT

Origin: Sport of 'C-15' this sport was induced by application of the procedures set forth in U.S. Pat. No. 4,724,276 to the seedling parent.

Classification:

*Botanic.*—*Euphorbia pulcherrima* Willd.

*Common name.*—Poinsettia.

*Cultivar name.*—'293'.

Form: Shrub. Height: Short to medium, shorter than 'C-15' grown under similar conditions.

Growth habit: As a single stemmed plant, upright and self-branching, with several axillary flowering branches. I observed 3 plants in a pot with an overall height of 41 cm. and an overall width of 50 cm. The bract diameter of individual flowers was 30 cm. Flower bracts are distinctly more upright than those of cultivar '293'.

Branching: Poinsettia '293' has self-branching traits. Axillary branches will develop and terminate in a flower without pinching. It may be desirable to pinch '293' and remove all terminal dominance. Then, as many as 8–10 axillary branches will develop uniformly and at a faster rate. In contrast, cultivar '268' produces 6–8 axillary branches after pinching.

Growth Rate: Rooting of stem cuttings occurs in 12–18 day under intermittent mist. The plant will flower in about nine weeks under continuous long night conditions and night temperatures of about 16–18 degrees C.

Foliage: The foliage is clean and uniformly medium green from bottom to top of the plant. The leaves are of medium size, leaf blades typically being about 12–13 cm. long and about 10–12 cm. wide with leaf petioles about 7–8 cm. long.

*Leaf Shape.*—Typical leaves are ovate with obtuse bases and acuminate tips. Leaf margins are either entire or lobed with 1 or 2 indentations on each side of the leaf blade.

*Color.*—Upper side — Green, near RHS 147A. Underside — Green, between RHS 138A and RHS 138B.

*Retention.*—The foliage lasts extremely well even under low light intensities in the consumer's home.

Bracts: Generally there are 18–24 uniformly colored bracts of various sizes subtending the cyathia. The primary bracts have blades typically 16–17 cm. long and 12 cm. wide with petioles about 3–4 cm. long.

*Shape:* Bracts are mostly ovate to elliptic and obovate with acute bases and acuminate tips. Primary bracts are lobed with 1 or 2 indentations on either side of the bract. Secondary bracts have entire margins.

*Color.*—Upper side — Orange red, near RHS 44A. Underside — Light red, near RHS 50A. This color is different from the bright red bract color of cultivar '268'.

Flowers: Generally, 15–21 cyathia (flowers) are present when the plant is in full bloom. Each cyathium is about 7–8 mm long and about 5 mm wide, light green in color and fringed with red at the distal end. One or two yellow nectar cups protrude from the side of each cyathium. The flower pedicel is also green and about 5–6 mm in length. The stamens protruding from the cyathia are red. Stems are unusually thick and stiff. Stems of cultivar '268' are more flexible and not comparably thick.

What is claimed is:

1. A new and distinct Poinsettia cultivar, substantially as herein shown and described, characterized by its orange red flower bracts, prolific branching and erect bract presentation.

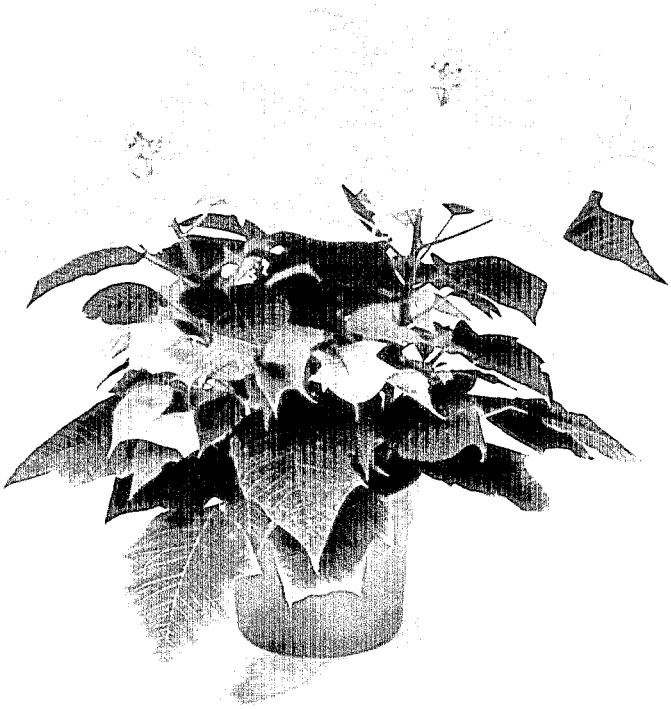
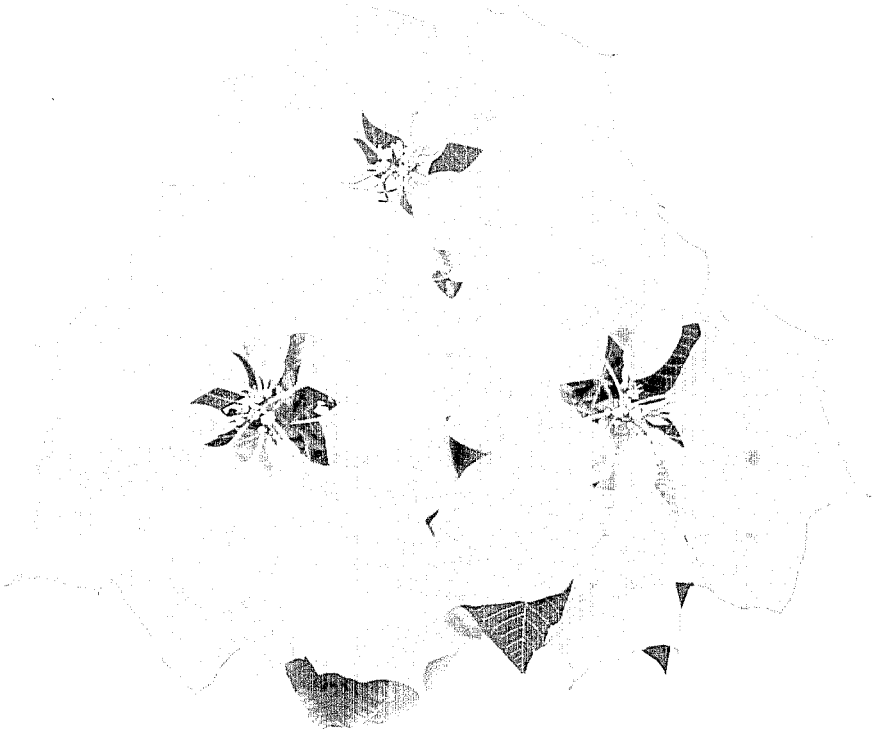

* * * * *